United States Patent [19]
DesLauriers et al.

[11] Patent Number: 5,221,534
[45] Date of Patent: Jun. 22, 1993

[54] HEALTH AND BEAUTY AID COMPOSITIONS

[75] Inventors: Paul J. DesLauriers, Conroe; William J. Heilman, Houston, both of Tex.

[73] Assignee: Pennzoil Products Company, Houston, Tex.

[21] Appl. No.: 649,196

[22] Filed: Feb. 4, 1991

Related U.S. Application Data

[63] Continuation of Ser. No. 343,273, Apr. 26, 1989, abandoned.

[51] Int. Cl.⁵ .................... A61K 31/74; A61K 7/02
[52] U.S. Cl. .................... 424/78.03; 424/59; 424/65; 424/78.18; 424/401
[58] Field of Search .......... 424/78, 78.03, 78.18, 424/65, 59, 401

[56] References Cited

U.S. PATENT DOCUMENTS

| | | | |
|---|---|---|---|
| 3,395,169 | 7/1968 | Mitchell | 260/448.2 |
| 3,574,827 | 4/1971 | Beerbower | 424/83 |
| 3,733,403 | 5/1973 | Chen | 424/83 |
| 3,867,533 | 2/1975 | Schmolka | 424/65 |
| 3,928,558 | 12/1975 | Cheeseman et al. | 424/47 |
| 4,061,780 | 12/1977 | Yoshida et al. | 424/358 |
| 4,164,563 | 8/1979 | Chang | 424/83 |
| 4,268,502 | 5/1981 | Martin | 424/83 |
| 4,387,090 | 6/1983 | Bolich, Jr. | 424/70 |
| 4,465,663 | 8/1984 | Schmolka | 424/65 |
| 4,563,346 | 1/1986 | Decker | 424/59 |
| 4,600,030 | 7/1986 | Newman | 132/88.5 |
| 4,659,562 | 4/1987 | Arraudeau et al. | 424/63 |
| 4,673,571 | 6/1987 | Mahieu et al. | 424/70 |
| 4,678,664 | 7/1987 | Schmolka | 424/65 |
| 4,721,579 | 1/1988 | Kim | 252/79 |
| 4,798,853 | 1/1989 | Handlin, Jr. | 523/173 |

FOREIGN PATENT DOCUMENTS

0224389 3/1987 European Pat. Off. .
WO88/00603 1/1988 PCT Int'l Appl. .

Primary Examiner—Thurman K. Page
Attorney, Agent, or Firm—Lowe, Price, LeBlanc & Becker

[57] ABSTRACT

Health and beauty aid compositions comprise one or more health and beauty aid components contained in a gel comprising a mineral oil containing from blends of di- and triblock copolymers based on synthetic thermoplastic rubbers.

13 Claims, 3 Drawing Sheets

DIBLOCK + TRIBLOCK (AB)ₙ

HEALTH AND BEAUTY AID COMPOSITIONS

This application is a continuation application of application Ser. No. 07/343,273, filed Apr. 26, 1989 now abandoned.

TECHNICAL FIELD

This invention relates to health and beauty aid compositions in the form of gels and more particularly relates to heterophase thermally reversible mineral oil gels, preferably white oil gels, useful as vehicles for health and beauty aids such as cosmetics. The compositions contain blends of block copolymers, the copolymers being preferably derived from styrene-rubber block copolymers.

BACKGROUND ART

The current methodology for producing mineral oil containing gels includes the use of metal soaps, surfactants (microemulsions), homopolymers, ionic homo- and copolymers and block copolymers. Some common gelling agents for cosmetic oil systems are fatty acid soaps of lithium, calcium, sodium, aluminum, zinc and barium. A number of homo- and copolymers have been used to gel hydrocarbon systems at certain polymer treatment levels including atactic ethylene-propylene. Homopolymers or copolymers which have pendant salt groups also form ion rich aggregates in a non-polar matrix. The ionic interaction and resultant polymer properties of these compositions, however, are dependent on the type of polymer backbone, type of ionic moiety and type of cation. Sulfonated polystyrenes exemplify this kind of system. Surfactant combinations have also been used to gel mineral oil/water systems. Surfactants are used at about 30 wt % to gel oil and to gel 1:4 oil and water mixtures. Nonionic surfactants such as polyoxyethylene sorbitan monoleates exemplify these type of systems.

Block copolymers are also known to form physical cross-links to gels by selective sulfation and subsequent phase separation of a particular block. Block systems including styrene-isoprene, styrene-butadiene and styrene ethylene oxide copolymers have been used for this purpose. For example, U.S. Pat. Nos. 3,867,533, 4,465,663, 4,678,664 and 4,721,579 of BASF disclose aqueous cosmetic gels prepared from polyoxybutylene-polyoxyethylene or polyoxyethylene-polyoxypropylene block copolymers. In addition, the following U.S. Patents disclose compositions which include various cosmetic formulations, some of which contain block polymers:

| | | |
|---|---|---|
| 3,395,169 | Mitchell | 1968 |
| 3,574,827 | Beerbower | 1971 |
| 3,733,403 | Chen | 1973 |
| 3,928,558 | Cheesman et al | 1975 |
| 4,061,780 | Yoshida et al | 1977 |
| 4,268,502 | Martin | 1981 |
| 4,387,090 | Bloich, Jr. | 1983 |
| 4,673,571 | Mahieu et al | 1987 |
| 4,563,346 | Deckner | 1986 |
| 4,600,030 | Newman | 1986 |
| 4,659,562 | Arraudeau et al | 1987 |

There remains a need in the art for new and improved gels of this type for health and beauty aids such as cosmetics in view of various problems with the prior art vehicles. For example the metal stearates in certain surfactants are potential irritants of the skin. Accordingly, in this invention, new improved and advantageous combinations of block copolymers are provided which produce heterophase thermally reversible mineral oil gels which have desirable properties for applications in the cosmetic and health and beauty aid industry.

DISCLOSURE OF THE INVENTION

It is accordingly one object of this invention to provide novel heterophase thermally reversible gel compositions which have advantageous properties when used in health and beauty aid applications.

A further object of the invention is to provide mineral oil gel compositions formed from certain blends of di- and triblock copolymers which have advantageous properties in cosmetics and health and beauty aid applications.

Still further objects of the invention include methods for preparation of heterophase thermally reversible mineral oil gels using certain blends of di- and triblock copolymers, the di- and triblock copolymers being preferably based on thermoplastic rubbers such as styrene-rubber block copolymers.

Also provided by the invention are health and beauty aid compositions comprising a cosmetically useful heterophase thermally reversible mineral oil gel formed from blends of di- and triblock copolymers based on synthetic thermoplastic rubbers and methods for applications of the composition.

Other objects and advantages of the present invention will become apparent as the description thereof proceeds.

In satisfaction of the foregoing objects and advantages, there is provided by the present invention a health and beauty aid composition which comprises:

(a) a hydrocarbon oil; and (b) a blend of polymers, said blend of polymers being selected from the group consisting of at least two of:
 1) a diblock copolymer;
 2) a triblock copolymer;
 3) a radial polymer;
 4) a multiblock polymer; and
 5) mixtures thereof;

said blend of polymers containing at least one diblock or triblock copolymer.

Also provided by the present invention are said health and beauty aid compositions in the form of novel heterophase thermally reversible gels which contain a hydrocarbon oil and the blend of polymers defined above in combination with an effective amount of at least one health and beauty aid ingredient.

BRIEF DESCRIPTION OF DRAWINGS

Reference is now made to the drawings accompanying the application wherein.

Figure 6:
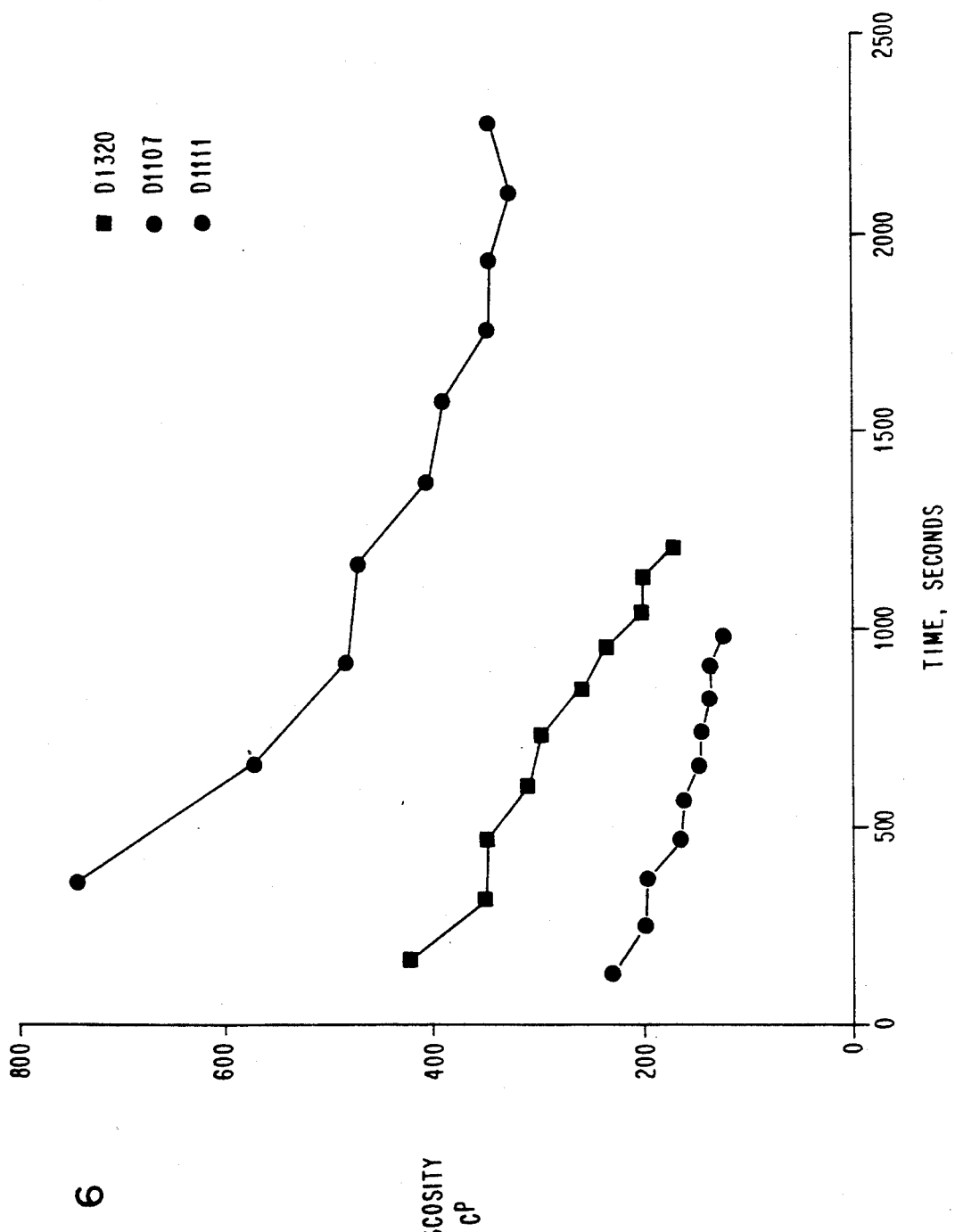

FIG. 6 is a graph illustrating a plot of the viscosity of hard gels as measured on a Mini Rotary Viscometer.

BEST MODE FOR CARRYING OUT THE INVENTION

It has been discovered according to the present invention that by controlling the degree of physical crosslinking exhibited in block copolymers, heterophase thermally reversible mineral oil gels can be formed which have desirable properties for cosmetic and health and beauty aid industries. According to this invention, the gel consistency is controlled by varying the amount, ratio and types of certain polymers, preferably di- and triblock copolymers, to provide gels which have desirable rheological properties and thus provide an excellent media or vehicle for the delivery of beauty aids such as mineral oils to the skin. Accordingly, the present invention provides a health and beauty aid composition which comprises a gel containing a beauty aid and a blend of polymers, preferably di- and triblock copolymers.

According to this invention it has been discovered that certain blends of polymers, preferably diblock copolymers, and triblock copolymers yield a gel which is not as tightly crosslinked as triblock components yield alone. The modified gel of the invention has the properties of maintaining a health and beauty aid material within the matrix of the polymer. The resulting gels are stable, pliable, won't break, are translucent, and do not exhibit syneresis. Product formation is achieved from block copolymers which will form three-dimensional networks or gels through physical crosslinks. Crosslinking in these block copolymers occurs due to the formation of submicroscopic particles of a particular block, referred to as domains. Crosslinking of the insoluble domains can be obtained by factors affecting the crosslink density of the networks including length of insoluble block domains, length of soluble block domains, and the number of crosslinkable sites. For example branched or star polymers will have more crosslinks than triblock or diblock polymers. The type of solvent or plasticizer to which the blocks are subjected will also affect these characteristics.

Figures 1A, 1B, 1C:
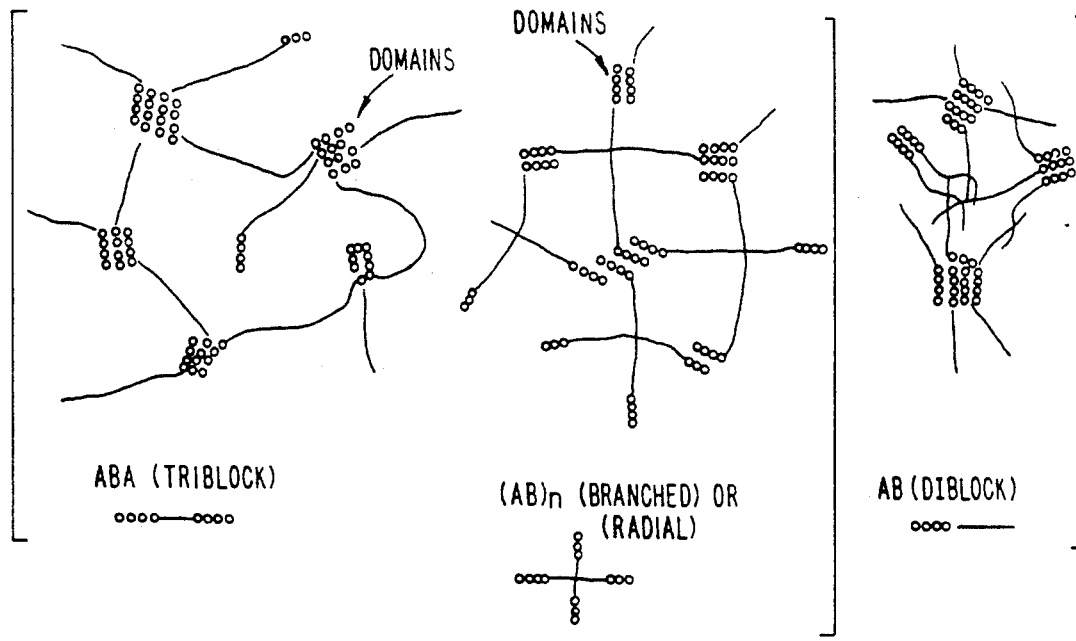
FIGS. 1A, 1B and 1C are illustrations of the cross-linking network and density of ABA triblock polymers, (AB)$_n$ branched and radial polymers, and AB diblock polymers.

FIG. 1 is an illustration of how this crosslinking occurs. In FIG. 1, the A blocks represent insoluble domains and B blocks represent soluble domains. FIG. 1A illustrates triblock copolymers which are mixtures of insoluble and soluble domains, FIG. 1B illustrates branched or radial mixtures of insoluble and soluble domains, and FIG. 1C illustrates diblock copolymers of insoluble and soluble domains.

Figures 2A, 2B:
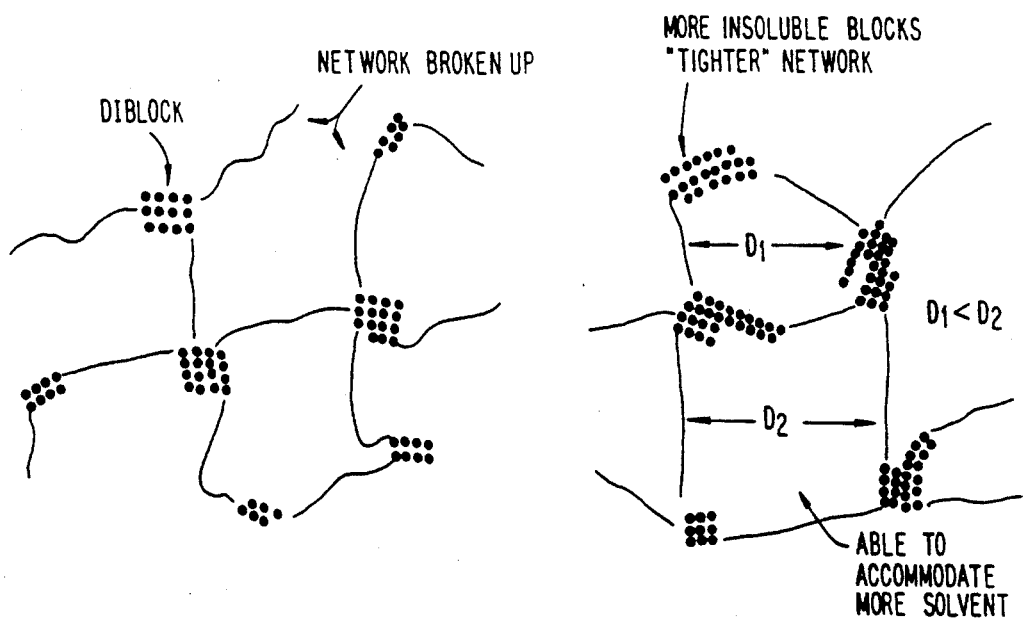
FIGS. 2A and 2B are illustrations of a diblock polymer and a mixture of diblock and triblock copolymers.

According to this invention it has been discovered that certain thermoplastic rubber copolymers are particularly suitable as gelling agents for cosmetic applications. It was discovered in this work that certain gels exhibit syneresis wherein the separation of liquid from the gel by contraction occurs by virtue of the concentration of the insoluble block present in the triblock copolymer. The higher the concentration of the insoluble block, as exemplified by styrene, the more phase separation and crosslinking will occur. However, according to this invention, it has further been discovered that the amount of syneresis which occurs can be controlled by mixing such systems with polymer blends such as diblock copolymers and with triblock copolymers which do not exhibit syneresis. FIG. 2 accompanying the application exemplifies this concept in showing in FIG. 2A a diblock copolymer with a network broken up, and in FIG. 2B, less insoluble blocks forming a looser network and the ability to accommodate more solvent.

In the present invention, it has been discovered that health and beauty aid compositions such as cosmetics can be prepared using this unique mixture of polymers such as blends of diblock and triblock copolymers in various combinations in order to provide health and beauty aid compositions having an improved combination of characteristics. The composition of the present invention utilizes a blend of polymers in combination with a hydrocarbon oil. Preferably the hydrocarbon oil is a cosmetic grade hydrocarbon oil and more preferably is white oil. The blend of polymers used comprises at least two polymers or copolymers selected from the group consisting of diblock polymers which contain at least two thermodynamically incompatible segments, triblock copolymers, radial polymers or copolymers, multiblock polymers or copolymers, and mixtures thereof, it being required however, that at least one diblock copolymer and/or triblock copolymer be present in the composition.

Preferably the blend is a mixture of diblock copolymers and triblock copolymers. By the expression thermodynamically incompatible with respect to the polymers is meant that the polymer contains at least two incompatible segments, for example at least one hard and one soft segment. In general in the diblock polymer, segments will be sequential with respect to hard and soft segments. In a triblock polymer, the ratio is two hard, one soft, two hard, one soft, etc. or a 2-1-2 copolymer. The multiblock polymers can contain any combination of hard and soft segments. In the composition, however, there must always be present at least one of the diblock or triblock copolymers. There must also be a combination which will provide both the hard and soft characteristics necessary for the composition. These characteristics are necessary in order to provide the controlled syneresis which is an essential part of the present invention in formation of the health and beauty aid gel compositions.

Figure 3:
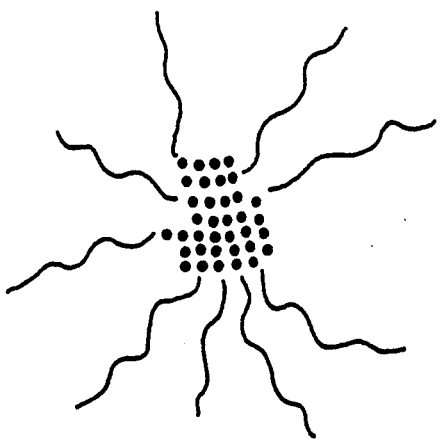
FIG. 3 is an illustration of the gelled form of a diblock polymer.
Figure 4:
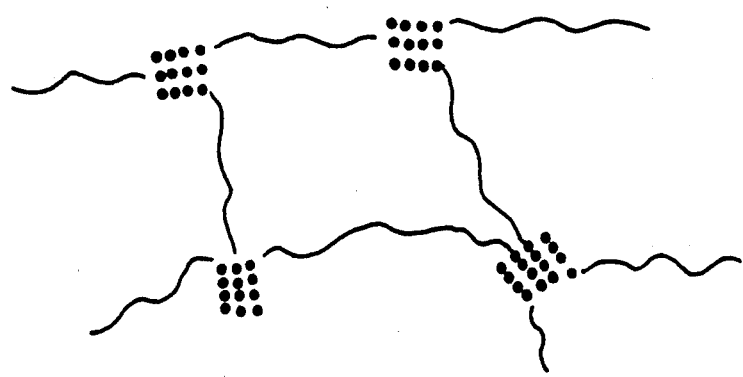
FIG. 4 is an illustration of the gelled form of a triblock polymer.
Figure 5:
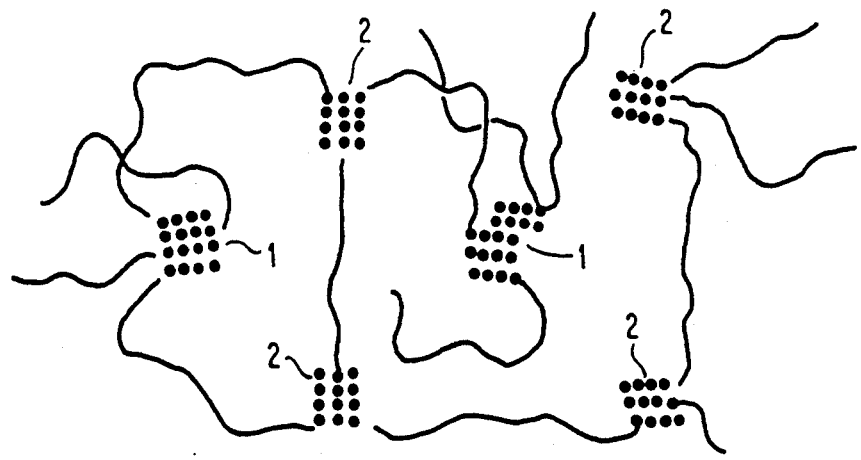
FIG. 5 is an illustration of a blend of the diblock polymer of FIG. 3 and the triblock polymer of FIG. 4 to form a blend in accordance with the compositions of the present invention.

In the compositions, the oil is contained within the polymer network formed by the polymer blend. Such networks are shown in FIGS. 1A, 1B and 1C and 2A and 2B. This is also illustrated in FIGS. 3, 4 and 5. In FIG. 3, there is shown a diblock polymer which is an AB or styrene butadiene diblock polymer. FIG. 4 is a triblock polymer or a styrene butadiene styrene polymer. Both of these polymers are linear polymers.

A preferred product of the present invention is illustrated by FIG. 5, which is a combination of a diblock polymer and a triblock polymer. As illustrated, this combination comprises repeating units of one diblock polymer followed by two triblock polymers in series. Thus, in FIG. 5, the numeral 1 indicates the triblock polymer portion and the numeral 2 indicates the diblock polymer portion.

Commercially available thermoplastic rubber type polymers which are especially useful in forming the compositions of the present invention are sold under the trademark Kraton ® by Shell Chemical Company. The Kraton ® rubber polymers are described as elastomers which have an unusual combination of high strength and low viscosity and a unique molecular structure of linear diblock, triblock and radial polymers. Each molecule of the Kraton ® rubber is said to consist of block segments of styrene monomer units and rubber monomer units. Each block segment may consist of 100 monomer units or more. The most common structure is the linear ABA block type; styrene-butadiene-styrene (SBS) and styrene-isoprene-styrene (SIS), the Kraton ® D rubber series. A second generation polymer of this series is the Kraton ® G series which are styrene-ethylene-butylene-styrene type (S-EB-S) polymers. Diblock polymers include the ABA type and the SB, styrene-ethylenepropylene (S-EP) and (S-EB). The ABA structure of the Kraton ® rubber molecule has polystyrene endblocks and elastomeric midblocks. This series of polymers is sold commercially and indicated as being major compounding ingredients or additives in adhesives, sealants and coatings, asphalt modification for roads and roofing, polymer modification, thermoset modification, and oil modification including use as viscosity index improvers, greases and gels. The Kraton ® G rubbers are indicated as being compatible with paraffinic and naphthionic oils and the triblock copolymers are reported as taking up more than 20 times their weight in oil to make a product which can vary in consistency from a "Jello" to a strong elastic rubbery material depending on the grade and concentration of the rubber. The gels are indicated as being used for applications as varied as cable filling or flooding compounds, toys and even strippable sealants and coatings. Certain grades of the Kraton ® D series are also indicated as being useful as viscosity modifiers for formulating multi-grade motor oils.

Published International Patent Application No. W88-00603, published Jan. 28, 1988, by Francis et al also describes block copolymers which can be used as one or more components in the present invention. These block copolymers are described as gels or gelloid liquid extended polymer compositions which can comprise an intimate mixture of a block copolymer containing relatively hard blocks and relatively elastomeric blocks, the additional polymer or copolymer material having at least partial compatibility with and a higher glass transition softening or melting temperature than the hard blocks of the block copolymer, and at least 500 parts by weight of extender liquid per 100 parts of the block copolymer, the liquid being present to extend and soften the elastomeric blocks of the block copolymer. The extender liquid can be a hydrocarbon oil and/or a synthetic oil. The gels or gelloid compositions are of the type which can be used in the compositions of the present invention and the entire disclosure of this published application is incorporated herewith.

The Francis et al published International Patent Application also refers to Published European Patent Application No. 224389 of Garmarra et al, published Jun. 3, 1987. This European patent application discloses styrene-diene block copolymer compositions and in particular discloses a mixture of triblock copolymers and a hydrocarbon oil wherein the mixture of triblock copolymers comprises a triblock polymer having (a) styrene to ethylene-butylene ratio of 14 to 30 styrene blocks to 70 to 86 ethylene-butylene blocks, and (b) ethylene-butylene ratio of 31 to 35 styrene blocks to 65 to 69 ethylene-butylene blocks, and wherein the ratio of copolymer A to copolymer B is from about 15 to 85 to about 85 to 15. These compositions are said to be particularly useful as sealing materials. Block copolymers of the type described in this published European application may also be used in the compositions of the invention and the disclosure of European Patent Application No. 224389 is incorporated herein by reference.

According to the present invention, health and beauty aid compositions such as cosmetic compositions are provided which comprise mixtures or blends which contain at least one diblock or triblock copolymer and one or more effective cosmetic ingredients. The blend of diblock and triblock polymers is formed from the diblock and triblock polymers described above. The blend of polymers comprises at least two components selected from the group consisting of diblock copolymers, triblock copolymers, radial copolymers, multiblock polymers, and mixtures thereof. However, there must be present in the composition at least a diblock or triblock copolymer. Preferred compositions will contain both diblock and triblock copolymers. Preferred polymer blends comprise from about 5 to 95 wt % of diblock polymer to 95 to 5 wt % of triblock polymer. Preferably there is present about 20 to 80 wt % of diblock copolymer to 80 to 20 wt % of triblock copolymer. More preferably, the diblock and triblock polymers are blended in the ratio of 40 to 60 wt % to 60 to 40 wt %.

In the preferred embodiment of the present invention, the blend of diblock and triblock polymers is formed in admixture with a carrier vehicle such as a natural or synthetic hydrocarbon oil or mixture thereof. Such hydrocarbon oils should have characteristics which will cause them to remain liquid at temperatures ranging from 0° C. up to about 200° C. for almost all applications. The hydrocarbon oil may be a paraffinic oil, a napthenic oil, natural mineral oil or the like. White oil is especially preferred.

When formed into gels, the mixture or blend of copolymers, will comprise about 1 to 20 wt % of the total weight. Preferably the total weight of polymer contained in the oil will range from about 5 to 15 wt %. Solvents which may be added to dilute the gel and form lotions and other flowable compositions comprise isopropyl myristate, isopropyl palmitate, silicones, organic esters, and the like. The commercially available Finsolv TN ™ is a particularly preferred solvent. Finsolv TN ™ is a benzoate $C_{12}$–$C_{15}$ ester available from Finetex, Inc., Elmwood Park, N.J.

The compositions of the invention are prepared by blending into the hydrocarbon oil the mixture or blend of diblock and/or triblock or other copolymers in the desired amounts. The amounts of each copolymer and the amount of the mixture contained in the hydrocarbon oil will determine the final form of the gel. The gel may range from a fragile gel through flexible gels and firm gels. The gel may also be transparent, translucent, or opaque depending on the ingredients.

The gel is formed by blending the polymers and oil and heating to 50° to 90° C. to dissolve the polymer blend in the oil. Mixing may be carried out in any conventional manner. On cooling, the gel forms. The health and beauty aid ingredient(s) may be added at any time. Preferably, the ingredient is added initially so that it dissolves when the composition is heated. Alternatively, a formed gel can be heated to reform the solution, the ingredient is added, and the gel allowed to reform on cooling.

The composition may contain an effective amount of one or more health and beauty aid ingredients. By health and beauty aid ingredients is meant any material which can be applied topically to the human skin or any part thereof for cleansing, beautifying, promoting attractiveness, protecting, or altering the appearance of the skin but which does not alter or interfere with the physiologic competence of the human skin or body. Included within this definition are creams, lotions and the like for use as sun screen agents, fragrance oils, moisturizers, anti-perspirants, humectants, cosmetic oils, and the like. The composition may also contain other skin care cosmetic ingredients such as excipients, colorants, preservatives, diluents, surfactants, anti-wrinkle agents, and the like. By "effective amount" is meant that a sufficient amount of the ingredient is present to be effective for the indicated purpose in the composition. An effective amount may range from 0.001 to 10 wt. %.

The gel products of the present invention provide carrier vehicles for topical administration of various health and beauty aid and cosmetic materials to the skin. Thus, products can be incorporated into the gel which are applied to the skin to be absorbed, to form a film on the skin, to provide a cooling sensation, to treat dry skin or oily skin, to work a product into the skin, to alter the overall texture of the skin, or to change color. All of these effects are sought to be achieved by various health and beauty- aid products such as cosmetics. It is a feature of the present invention that the gels can be used for virtually any health and beauty aid purpose depending on the selection of the particular polymer combination and effective health and beauty aid ingredient.

Particularly preferred uses of the compositions of the present invention are for formation of soft gels and hard gels. Soft gels are particularly useful in waterproofing sunscreen compositions, makeup, mascara, etc. They are also useful in petrolatum-based products such as petroleum jelly, makeup foundation and night creams. They can also be used as substitutes for water-soluble polymers in products such as lip rouge-cream, eyeliner liquid and the like. They may also be used as a gelling agent in facial oils.

Hard gels have applications in areas such as toiletry sticks such as a matrix for clear or opaque stick products including deodorants, lipstick, analgesics, blushers, solid lotions and solid fragrances. Hard gels may also be used as non-absorbable flexible hydrocarbon gels and as stick insect repellents. It is clear that the composition of the invention has wide applications in various health and beauty aid compositions.

A preferred composition of the invention will contain from 2-6% of the polymer blend and from 94-98% of a suitable hydrocarbon oil, preferably white oil. The preferred polymer combination is a blend of diblock and triblock polymers of the Kraton ® type in a weight ratio of 2:1 to 1:3. The polymers preferably have a Brookfield viscometer viscosity using a Number 5 spindle at 25° C. of 300 to 60,000 cps.

The preferred composition of the present invention will utilize a polymer blend which has a cone penetration value in the range of 200–300 1/10 mm, as this value provides gels having the preferred characteristics. Cone penetration values are obtained used ASTM Test Method 0217.

The formulation for the products of the invention will comprise about 80–99% of the hydrocarbon oil or carrier vehicle, about 1–20% of the mixture of diblock and triblock polymers, and an effective amount, e.g., 0.001 up to 10, %, of one or more health and beauty aid ingredients.

In a particularly preferred embodiment of the invention, the composition comprises a blend of Kraton ® diblock and triblock copolymers as described herein in combination with a cosmetic oil, particularly natural or synthetic white oils which are known as having a smooth homogeneous consistency and which adhere efficaciously to the skin for many types of topical applications.

The following examples are presented to illustrate the invention but it is not to be considered as limited thereto. In the examples parts are by weight unless otherwise indicated.

In these examples, the diblock and triblock polymers used are Kraton ® polymers obtained from Shell Chemical Company.

EXAMPLE 1

In this example Drakeol-9 mineral oil was gelled using various Kraton ® thermoplastic rubbers at a rate of 5.0 wt %. Drakeol is U.S.P. mineral oil. A preliminary evaluation of the properties of these polymers and the resulting mineral oil gels is given in Table 1 below:

TABLE 1

| Kraton Code # | Block Type[1] | $\overline{M}_p{}^2$ | Styrene/ Rubber | Properties of Resulting Gel[3] |
|---|---|---|---|---|
| D 1102 | SBS | 80,000 | 28/72 | very firm gel[4] |
| D 1116 | (SB)$_n$ | 200,000 | 21/79 | very firm gel[4] |
| D 1184x | (SB)$_n$ | 260,000 | 30/70 | swellable polymer |
| D 4230x | (SB)$_n$ | 120,000 | 46/54 | swellable polymer |
| D 1107 | SIS | 160,000 | 14/86 | firm gel |
| D 1111 | SIS | 160,000 | 21/79 | firm gel |
| D 1320x | (SI)$_n$ | 85,000 | 10/90 | firm gel |
| G 1701x | SEP | 90,000 | 37/63 | very soft gel |
| G 1702x | SEP | 140,000 | 28/72 | soft gel |

[1](SBS) styrene-butadiene-styrene block copolymer. (SIS) styrene-isoprene-styrene block copolymer. (SEP) styrene-ethylene-propylene block copolymer. (SB)$_n$ styrene-butadiene or (SI)$_n$ styrene-isoprene multiarm (branched) copolymer.
[2]Peak Molecular Weight
[3]5.0 wt % Solutions
[4]Exhibited Syneresis In the above Table 1, it will be noted that mineral oil gels made from styrene-butadiene polymers identified as D1102 and D1116 produced a firm opaque gel topped by a layer of oil. The presence of the oil layer is indicative of high cross-link density. These gels are so highly cross-linked that mineral oil is squeezed out of the gel matrix. Styrene-isoprene/mineral oil gels made from the polymers D1107, D1111 and D1320 were firm, flexible, translucent and did not exhibit syneresis. Diblock styrene-ethylenepropylene copolymers G1701 and G1702 produced mineral oil gels that were soft, pliable and transparent. (SB)$_n$ block copolymers D1184 and D4230, having styrene/rubber ratios of 30/70 and 46/54 respectively, produced gummy swollen masses when placed in Drakeol-9. Of the two polymers D1184 appeared to be better solvated.

It is evident from these observations that the best products are made from Kraton ® D1107, D1111 and D1320 as these provide stable, firm mineral oil gels while G1701 and G1702 can be used to make soft mineral oil gels. It is recognized that the properties of a particular gel are dictated by the inherent properties of the cross-linking polymer such as molecular weight, block type and the amount of insoluble A block present in the polymer, so it is difficult to draw absolute correlations between these properties and the resulting gels.

In FIG. 6, the strength of the Kraton ® mineral oil gels are evaluated in the Mini Rotary Viscometer (MRV). These studies indicate that the Mini Rotary Viscometer can be used to characterize the tightness or cross-linked density of the gels. It will be noted from FIG. 6 that the gels evaluated are made from the polymers D1320, D1107, and D1111.

EXAMPLE 2

In these examples, screening experiments of block copolymer gellants were carried out. These screening experiments were conducted using several mixtures of Kraton ® thermoplastic rubbers dissolved in Drakeol-9. These gels were prepared by dissolving the block copolymers indicated in the mineral oil at 50°–70° C. The solutions were then poured into aluminum tins and allowed to cool. The resulting gels were then subjectively evaluated for the amount of surface oiling which could be detected by touch. The characteristics of the polymers, the polymer solutions, the ratio of polymer solution used, and the total weight percent of polymer and oil, were evaluated by subjective evaluation of the gel. From this table it will be noted that the gels have various characteristics ranging from fragile gels through flexible gels and the like.

The screening of Kraton ® thermoplastic rubbers for use as clear mineral oil gellants in cosmetic and home beauty aid products was carried out by screening Kraton ® block copolymers by visually examining gels made by dissolving a 5 wt % polymer in Drakeol-9. Several di-, tri- and radial block copolymers were examined. The results of these examinations are set forth in Tables 2, 3 and 4, respectively. As will be noted from the tables, it was found in general that the opacity and firmness of the gels examined increased with increasing amounts of the styrene block and cross-linked density. All of the gels examined were found to be thermo-reversible at temperatures of 30°–50° C. with the exception of diblock polymer D1118. The diblock copolymer D1118 discolored in mineral oil and gave a rheopectic fluid. It was found that when the translucent viscous liquid is gently stirred or sheared, a soft gel material is formed.

The macro-micelle systems obtained from the diblock copolymers G1701X and G1702X formed clear soft gels which appear useful in cosmetic and home beauty aid products as water proofing agents or viscosity modifiers in mineral oil based systems. These polymers will also serve as backbones on which other additives may be grafted, as in sun screening agents. Of the tri- and radial block copolymers examined, only the styrene-ethylene-butylene-styrene triblock copolymers G1650 and G1652 gave clear firm gels.

The following Tables 2, 3 and 4 describe selected properties of Kraton ® diblock polymers in Table 1, Kraton ® triblock polymers in Table 2, and Kraton ® branched or radial block copolymers in Table 3. As will be noted from these tables, the first column is the code number assigned to the particular Kraton ® material as obtained from the manufacturer, Shell Chemical Company. In the block type, SB means styrene-butadiene, SEP means styrene-ethylene-propylene, SEBS means styrene-ethylene-butylene-styrene, SBS means styrene-butadiene-styrene, SIS means styrene-isoprene-styrene, SI means styrene-isoprene branched copolymer, and SB means styrene-butadiene copolymer. These tables also describe the block type, the melting point of the polymer, the styrene/rubber relationship, the melting point of the styrene block, and the properties of resulting gels in the last column. Kraton ® copolymers G1652 and G1650 are preferred components. These tables are as follows:

TABLE 2

Selected Properties of Kraton ® Diblock Copymers (AB)

| Kraton ® Code # | Block Type | $\overline{M}p$ | Styrene/Rubber | $\overline{M}p$ of Styrene Block | Properties of Resulting Gels |
|---|---|---|---|---|---|
| D1118 | SB | 50,000 | 30/70 | 15,000 | Very soft, translucent (rheopectic) |
| G1701X | SEP | 90,000 | 37/63 | 33,700 | Very soft, transparent |
| G1702X | SEP | 140,000 | 28/72 | 39,200 | Soft, Transparent |

TABLE 3

Selected Properties of Kraton ® Triblock Copolymers (ABA)

| Kraton ® Code # | Block Type | $\overline{M}p$ | Styrene/Rubber | $\overline{M}p$ of Styrene Block | Properties of Resulting Gels |
|---|---|---|---|---|---|
| G1652 | SEBS | 50,000 | 30/70 | 7,500 | Firm, Transparent |
| G1650 | SEBS | 60,000 | 30/70 | 9,000 | Firm, Transparent |
| D1102 | SBS | 80,000 | 28/72 | 11,200 | Contracted, Opaque |
| D1107 | SIS | 160,000 | 21/79 | 16,800 | Firm, Translucent |
| D1111 | SIS | 160,000 | 14/86 | 11,200 | Firm, Translucent |

TABLE 4

Selected Properties of Kraton ® Branched (or Radial) Block Copolymers (AB)$_n$

| Kraton ® Code # | Block Type | $\overline{M}p$ | Styrene/Rubber | $\overline{M}p$ of Styrene Block | Properties of Resulting Gels |
|---|---|---|---|---|---|
| D1320 | (SI) | 140,000 | 10/90 | 14,000 | Firm, Translucent |
| D1116 | (SB) | 200,000 | 21/79 | 42,000 | Contracted, Opaque |
| D1184X | (SB) | 260,000 | 30/70 | 78,000 | Swellable Polymer |
| D4230X | (SB) | 120,000 | 46/54 | 55,000 | Slightly Swellable Polymer |

EXAMPLE 3

The following Table 5 illustrates selected properties of mixtures of Kraton ® triblock and diblock polymers and exemplifies those polymers which are preferred for use in the present compositions of the present invention. These polymers, through evaluation, were found to provide useful gels for use in the compositions of the invention. These screening experiments were conducted using several mixtures of Kraton ® thermoplastic rubbers in Drakeol-9. The gels were prepared by dissolving the block copolymers in the mineral oil at 50°–70° C. after which the solutions were poured into aluminum tins and allowed to cool. The resulting gels were then subjectively evaluated for the amount of surface oiling which could be detected by touch, the results of which are given in Table 5. The results show that either approach can be used to control the amount of residual surface oil on the gels tested. Evaluation of these gels suggests that a hand lotion bar product contains ~6–10 wt % polymers.

TABLE 5

Subjective evaluation of anhydrous mineral oil gels made from Kraton ® thermoplastic rubbers in Drakeol ® 9.

| Kraton ® Polymers | Polymer Type[a] | Wt % of Each Polymer Solution | Ratio of Polymer Solution Used | Total Wt % Polymer in Oil | Subjective Evaluation of Gel |
|---|---|---|---|---|---|
| D1102 | SBS | 5 | — | 5.0 | Fragile gel, exhibits syneresis |
| D1102/ G1652 | SBS/ SEBS | 5/5 | 9/1 | 5.0 | Fragile gel, less oil on surface than previous gel |
| D1102/ G1652 | SBS/ SEBS | 5/5 | 5/1 | 5.0 | Flexible gel, slight oiling of surface |
| D1102/ G1652 | SBS/ SEBS | 5/5 | 2/1 | 5.0 | Flexible gel, very little oil on surface |
| D1102/ G1652 | SBS/ SEBS | 5/5 | 1/1 | 5.0 | Flexible gel, no oil on surface |
| D1102/ G1652 | SBS/ SEBS | 10/5 | 2/1 | 15.0 | Strong flexible, tacky gel, slight oiling of surface |
| G1652 | SEBS | 10 | — | 10.0 | Flexible gel, no oil on surface |
| G1652 | SEBS | 15 | — | 15.0 | Flexible gel, no oil on surface |
| G1652/ G1701 | SEBS/ SEP | 15/5 | 1/1 | 10.0 | Flexible, tacky gel, slight oiling of surface |
| G1652/ G1701 | SEBS/ SEP | 3.5/3.5 | 1/1 | 3.5 | Soft tacky gel |

[a]SBS = Styrene-butadiene-styrene; SEBS = Styrene-ethylene butylene-styrene; SEP = Styrene-ethylene propylene.

EXAMPLE 4

The following Table 6 evaluates the consistency of white mineral oil gels made from a composition which contains 10% of the indicated block copolymer contained in 90% of the white oil, in this case Drakeol 5. In the following Table 6, it will be noted that the cone penetration value for the two Kraton ® copolymers selected ranges from 147, which contains only triblock polymer, to 313, which contains only diblock polymer.

The following Table 7 illustrates cone penetration values obtained using blends of diblock polymers and Table 8 illustrates cone penetration values obtained with blends only of triblock polymers. From Tables 7 and 8 it will be noted that the cone penetration values of triblock polymers are generally less than 160, whereas those with the diblock polymers are generally above 300. The combination results in the preferred cone penetration blends of between 200 and 300.

TABLE 6

CONSISTENCY OF WHITE OIL GELS MADE FROM 10% BLOCK COPOLYMER IN DRAKEOL ® 5

| G1702 % DIBLOCK | G1652 % TRIBLOCK | CONE PENETRATION VALUE |
|---|---|---|
| 10 | 0 | 313 |
| 7 | 3 | 283 |
| 5 | 5 | 241 |
| 3 | 7 | 258 |
| 0 | 10 | 147 |

TABLE 7

CONSISTENCY OF WHITE OIL GELS MADE FROM 10% BLOCK COPOLYMER IN DRAKEOL ® 5

| % DIBLOCK G1701 | G1702 | CONE PENETRATION VALUE[1] |
|---|---|---|
| 10 | — | 330 |
| 6.7 | 3.3 | 307 |
| 5.0 | 5.0 | 302 |
| 0 | 10.0 | 313 |

[1]Value has 10% error

TABLE 8

CONSISTENCY OF WHITE OIL GELS MADE FROM 10% BLOCK COPOLYMER IN DRAKEOL ® 5

| % TRIBLOCK G1G52 | G1650 | CONE PENETRATION VALUE[1] |
|---|---|---|
| 10 | 0 | 147 |
| 6.7 | 3.3 | 156 |
| 3.3 | 6.7 | 152 |
| 0 | 10.0 | 139 |

[1]Value has 10% error

EXAMPLE 5

In this example cone penetration values are derived from blends of diblock and triblock polymers over various ranges. The copolymers used are Kraton ® polymers identified as G1701 as a diblock copolymer and G1652 and G1650 as triblock polymers. This Table 9 as well as the following Table 10 illustrate cone penetration values obtained using various blends of different Kraton ® polymers.

TABLE 9

CONSISTENCY OF WHITE OIL GELS MADE FROM 10% BLOCK COPOLYMER IN DRAKEOL ® 5

| % DIBLOCK (G1701) | % TRIBLOCK (G1652) | % TRIBLOCK (G1650) | CONE PENETRATION VALUE[1] |
|---|---|---|---|
| 10 | 0 | — | 330 |
| 6.7 | 3.3 | — | 198 |
| 5.0 | 5.0 | — | 270 |
| 3.3 | 6.7 | — | 179 |
| 0 | 10 | — | 147 |
| 10 | — | 0 | 330 |
| 6.7 | — | 3.3 | 163 |
| 5.0 | — | 5 | 197 |
| 0 | — | 10 | 139 |

[1]10% error in value

TABLE 10

CONSISTENCY OF WHITE OIL GELS MADE FROM 10% BLOCK COPOLYMER IN DRAKEOL ® 5

| % DIBLOCK (G1702) | % TRIBLOCK (G1652) | % TRIBLOCK (G1650) | CONE PENETRATION VALUE[1] |
|---|---|---|---|
| 10 | 0 | — | 313 |
| 6.7 | 3.3 | — | 283 |
| 5.0 | 5.0 | — | 241 |
| 3.3 | 6.7 | — | 258 |
| 0 | 10 | — | 147 |
| 10 | — | 0 | 313 |
| 6.7 | — | 3.3 | 214 |

TABLE 10-continued

| CONSISTENCY OF WHITE OIL GELS MADE FROM 10% BLOCK COPOLYMER IN DRAKEOL ® 5 | | | |
|---|---|---|---|
| % DIBLOCK (G1702) | % TRIBLOCK (G1652) | % TRIBLOCK (G1650) | CONE PENETRATION VALUE[1] |
| 5.0 | — | 5.0 | 216 |
| 0 | — | 10 | 139 |

[1]10% error in value

EXAMPLE 6

In this Example, the compatibility of a gel made from 3 wt % of Kraton 1702 and 2 wt % Kraton 1650 in Drakeol 5 is studied with various cosmetic components. The components and their amounts are identified in Table 11. In the evaluation in Table 11, the positive sign denotes that separation of the sample did not occur either on mixing or after cooling to 0° C. for 24 hours, and subsequent heating at 50° C. for 24 hours.

TABLE 11

| COMPATIBILITY OF GELS WITH VARIOUS COSMETIC COMPONENTS | | | |
|---|---|---|---|
| COMPONENT | 2 WT % | 10 WT % | 50 WT % |
| Emollients | | | |
| Finsolv TN TM (Benzoate $C_{12}$-$C_{14}$ ester) | + | + | + |
| White Oil | + | + | + |
| Sunflower Oil | + | + | + |
| Dimethicone | + | | |
| Cyclomethicone | + | + | |
| Preservative | | | |
| Isopropanol | + | + | |
| Phenol | + | | |
| Organic Humectant | | | |
| Propylene Glycol | + | + | |
| Glycerin | + | + | |
| Water | + | | |

[1])Positive sign denotes that separation of sample did not occur.

EXAMPLE 7

In this example there is set forth information for determining preferred formulations with preferred viscosities and aesthetic properties. This work was carried out by use of a software program called ECHIP, a copyrighted program of Expert in a Chip, Inc. In these experiments, the ECHIP Design was used for a deashing lotion formulation. The formulation contained two gel components: Gel 1, the diblock polymer Kraton 1702, and Gel 2, the triblock polymer Kraton 1650. The other components are Drakeol, a white oil, and Finsolv TN~, a benzoate $C_{12}$-$C_{15}$ ester solvent.

In this work the components were utilized within the concentration ranges of Table 12.

TABLE 12

| Components | Conc. Range (WT %) |
|---|---|
| Gel 1 (Diblock) | 2.7-3.0 |
| Gel 2 (Triblock) | 1.3-3.0 |
| Drakeol 5 | 0-96 |
| Drakeol 35 | 0-96 |
| Finsolv TN~ | 0-30 |

The gels are used at a maximum of 6% in the formulation for various formulations. A total of 25 blends were studied using the values set forth in Table 13. Thereafter, the characteristics of these 25 blends were incorporated into the ECHIP triangle of Table 14. The fit in the triangle of Table 14 was within the effects table of this program. The data from the triangle of Table 14 was then interpreted to provide the viscosity (log) data of Table 15, the log being further converted to centipoises.

TABLE 13

| | ECHIP . . . design | | | | |
|---|---|---|---|---|---|
| | GEL1 | GEL2 | DRAKEOL5 | DRAKEOL35 | FINSOLV |
| 1 | 0.02680 | 0.01320 | 0.92160 | 0.00000 | 0.03840 |
| 2 | 0.03000 | 0.01320 | 0.00000 | 0.91853 | 0.03827 |
| 3 | 0.02840 | 0.03000 | 0.90394 | 0.00000 | 0.03766 |
| 5 | 0.03000 | 0.03000 | 0.90240 | 0.00000 | 0.03760 |
| 6 | 0.02680 | 0.01320 | 0.00000 | 0.92160 | 0.03840 |
| 7 | 0.03000 | 0.01320 | 0.66976 | 0.00000 | 0.28704 |
| 8 | 0.03000 | 0.03000 | 0.00000 | 0.65800 | 0.28200 |
| 9 | 0.03000 | 0.01320 | 0.91853 | 0.03827 | 0.00000 |
| 10 | 0.02680 | 0.03000 | 0.66024 | 0.00000 | 0.28296 |
| 11 | 0.02680 | 0.01320 | 0.33600 | 0.33600 | 0.28800 |
| 13 | 0.02840 | 0.02160 | 0.47500 | 0.47500 | 0.00000 |
| 14 | 0.03000 | 0.01320 | 0.45926 | 0.35402 | 0.14352 |
| 16 | 0.03000 | 0.01320 | 0.00000 | 0.66976 | 0.28704 |
| 17 | 0.02680 | 0.02160 | 0.00000 | 0.66612 | 0.28548 |
| 19 | 0.03000 | 0.03000 | 0.65800 | 0.00000 | 0.28200 |
| 20 | 0.02680 | 0.02160 | 0.91354 | 0.00000 | 0.03806 |
| 1 | 0.02680 | 0.01320 | 0.92160 | 0.00000 | 0.03840 |
| 2 | 0.03000 | 0.01320 | 0.00000 | 0.91853 | 0.03827 |
| 3 | 0.02840 | 0.03000 | 0.90394 | 0.00000 | 0.03766 |
| 5 | 0.03000 | 0.03000 | 0.90240 | 0.00000 | 0.03760 |
| 9 | 0.03000 | 0.01320 | 0.91853 | 0.03827 | 0.00000 |
| 13 | 0.02840 | 0.02160 | 0.47500 | 0.47500 | 0.00000 |
| 15 | 0.03000 | 0.03000 | 0.03760 | 0.90240 | 0.00000 |
| 15 | 0.03000 | 0.03000 | 0.03760 | 0.90240 | 0.00000 |
| 21 | 0.02900 | 0.02200 | 0.66400 | 0.21400 | 0.07100 |
| 22 | 0.02900 | 0.02200 | 0.56900 | 0.28500 | 0.09500 |
| 23 | 0.02900 | 0.02200 | 0.42700 | 0.38000 | 0.14200 |
| 24 | 0.02900 | 0.02200 | 0.33200 | 0.45100 | 0.16600 |
| 25 | 0.02900 | 0.02200 | 0.19000 | 0.54600 | 0.21400 |

TABLE 14

```
                    E C H I P
            0.00    * H *    0.94
                    / H H ,
                   / . H H H H
                  / . . H H H H H
       5        / . . . H H . . . .        D
    L 0.23    * . . . . . . . . G G , *  0.71  R
       O     / G . . . . . G G G , F F .         A
       E    / G G G . G G G G , , F . E , D        K
       K   / G G G G G G G , , F . . E , D C ,       E
       A  / G G G G G G , , F F . E , D . C B . <      O
    R 0.47 * G G G G G , , , F . . E , D C , B A < < < *  0.47  L
       D   / , G G , , , , F F . E , D . C , . A < < < < <      3
          / , , , , , , F F . . E , D . , B . < < < < < < <      5
         / , , , , , , F F . E , D . C , B A < < < < < < < < <
        / , , , , , F F . . E , D . C B . A < < < < < < < < < < <
```

TABLE 14-continued

```
0.70  *,,,,,FF.EE,D.,B.<<<<<<<<<<<<<<<*  0.24
      /,,,,FF..E,D.C,BA<<<<<<<<<<<<<<<<
      /,,,,FF..E,D.C,.A<<<<<<<<<<<<<<<<<
      /,,,,FF.EE,D.CB.<<<<<<<<<<<<<<<<<<<
      /,,,,FF.EE,DC,B.<<<<<<<<<<<<<<<<<<<<
0.94  *,,,,FF.E,D.C,BA<<<<<<<<<<<<<<<<<<<<<<*  0.00
      **----------*----------*----------*----------**
      0.00        0.23        0.47        0.70        0.94
                             F I N S O L V
```

TABLE 15

| VISCOSITY | |
|---|---|
| (log) | cps |
| A = 2.698970 | 500 |
| . = 2.865980 | |
| B = 3.032990 | 1,079 |
| , = 3.200000 | |
| C = 3.367010 | 2,328 |
| . = 3.534020 | |
| D = 3.701030 | 5,024 |
| , = 3.868040 | |
| E = 4.035050 | 10,840 |
| . = 4.202060 | |
| F = 4.369070 | 23,392 |
| , = 4.536080 | |
| G = 4.703090 | 50,478 |
| . = 4.870100 | |
| H = 5.037110 | 108,920 |
| , = 5.204120 | |

GEL1 = 0.030
GEL2 = 0.030

EXAMPLE 8

The esthetics of the products were evaluated for the gels of the invention. The following Table 16 sets forth trends with respect to "Product Feel" during initial application, during rub-in, and after complete absorption of the product by the skin. "Product Feel" is set forth in Table 16 followed by a "Vocabulary Regarding Aesthetic Properties" of cosmetics.

TABLE 16

| PRODUCT FEEL |
|---|
| INITIAL APPLICATION |
| Pickup (Very Poor/Good/Excellent) |
| Slip (Slight/Medium/Much) |
| Cushion (Slight/Medium/Much) |
| Texture (Heavy/Medium/Light) |
| Texture (Grainy/Coarse/Smooth) |
| FEEL DURING RUB-IN |
| Change in Texture (Becomes Heavier/No Change/Becomes Lighter) |
| Lubricant Qualities (Tacky/Drags/Slides) |
| Spreadability (Very Poor/Good/Excellent) |
| Play Time (Prolonged/Medium/Short) |
| Absorption (Prolonged/Medium/Short) |
| AFTERFEEL |
| (Skin feel after complete absorption of Product |
| Smoothness (Poor/Good/Velvety Rich) |
| Friction (Tacky/Skids/Drags/Slight Drag/Slip) |
| Oiliness (Oily/Waxy/Dry) |
| Moistness (Dewy/Neutral/Dry) |

VOCABULARY REGARDING AESTHETIC PROPERTIES

Absorption - The skin's "taking-in" of a product. Descriptive words referring to absorption are "penetrate" and "soak-in".

Afterfeel - Describes the effect or sensation following the complete absorption of a product. Afterfeel is usually referred to initially 15 minutes after application and one hour after application. Some terms used to describe afterfeel are soft, smooth, greasy, dry, etc.

Consistency - The degree of looseness or firmness of a product sometimes referred to as viscosity. Terms associated with consistency are thick, thin, watery, runny, etc.

Cooling - A sensation either on application, during rub-in or an afterfeel that is colder than if nothing had been applied.

Cushion - A soft velvety slip that seems to have layers or thickness to it.

Drag - The sensation or feel that a product is hindered in its ability to move across the surface of the skin.

Dry

Dry Skin Feel - The way the skin feels after being washed with a strong soap. When dry is used to describe afterfeel. It would be the sensation as if nothing had been applied or no moisturization had taken place.

Dry Product Feel - Lack of the sensation of slip which is felt during rub-in. Dry as related to product can be both positive and negative depending upon the result desired.

Drying Time - The amount of time it takes a product to dry after application. This usually is measured in seconds and minutes.

Film - A slight coating felt during rub-in. When referring to afterfeel, it is a coating felt when the product is complete absorbed. The coating can be waxy, greasy, smooth, or velvety, etc.

Greasy - A large amount of heavy oiliness felt at any time during application or rub-in. When referring to afterfeel, it would be a heavy oil residue left on the skin.

Oily - Light greasiness, see above definition for greasiness.

Pickup - The ability of a product to be easily obtained in sufficient quantities from a jar (i.e., product cannot be runny or waxy).

Playtime - The amount of time necessary for a product to be worked into the skin beginning from application to absorption.

Rub-in - The action of working a product into the skin with the hand and the characteristics of this action.

Slip - An easy sliding motion felt during rub-in.

Tacky - Sticky to the touch.

Texture - Reference to the overall structure of the product either in appearance or fell, such as its body. Texture is described in words such as light, heavy, creamy, rich, silky, velvety, smooth, grainy, etc.

Warm - A sensation of heat felt either on application, during rub-in or as part of the afterfeel.

Waxy - A dry coating felt during rub-in or an afterfeel similar to the stroking of a candle.

Wet - A watery feel either on application or during rub.

Whitening - A visual effect obtained during rub-in whereas the product goes through a phase of being white before being absorbed. Sometimes referred to as soaping, lathering, or creaming.

As a result of these evaluations, the following Table 17 is provided to show trends in the properties of gels with respect to increasing amounts of components when evaluated for viscosity and esthetics.

TABLE 17

RESULTS INDICATE THE FOLLOWING TRENDS IN THE PROPERTIES OF WHITE OIL GELS WITH RESPECT TO INCREASING AMOUNTS OF COMPONENTS

| COMPONENT | VISCOSITY | ESTHETICS |
|---|---|---|
| Diblock/Triblock Gel* | + | + |
| Increasing amounts of Triblock Copolymer in mixture | + | − |
| Drakeol 35 | + | − |
| Cyclomethicone (Pentamer) | + | + |
| Finsolv TN | − | + |

*Formed from Kraton 1702 and Kraton 1650.

The invention has been described herein with reference to certain preferred embodiments. However, as obvious various thereon will become apparent to those skilled in the art, the invention is not to be considered as limited thereto.

We claim:

1. A health and beauty aid composition in gel form comprising an effective amount of one or more health and beauty aid components, about 80 to 99 wt. % of a hydrocarbon oil, and about 1 to 20 wt. % of a blend of at least two different polymer members selected from the group consisting of diblock copolymers, triblock copolymers, radial block copolymers and multiblock copolymers, with the proviso that there be contained in the composition at least one diblock copolymer or at least one triblock copolymer, with said at least one diblock copolymer or said at least one triblock copolymer comprising 5 to 95 wt. % of said blend of at least two different polymers, said diblock and triblock polymers comprising segments of styrene monomer units and rubber monomer units.

2. A health and beauty aid composition according to claim 1 wherein the blend of copolymers comprises at least one diblock copolymer and at least one triblock copolymer.

3. A composition according to claim 1 wherein the di- and triblock copolymers are derived from thermoplastic rubbers.

4. A composition according to claim 3 wherein the diblock polymers and triblock polymers contain insoluble portions and soluble portions and are thermoplastic rubbers.

5. A composition according to claim 1, further including a solvent selected from the group consisting of isopropylmyristate, isopropylpalmitate, silicones, benzoate esters, and mixtures thereof.

6. A composition according to claim 1 which comprises a blend of diblock polymers and triblock polymers contained in an amount of about 1-20 wt % in a hydrocarbon oil.

7. A composition according to claim 1 wherein the blend of polymers contains about 10-90 wt % of diblock polymer and about 90-10 wt % of triblock polymer.

8. A composition according to claim 1 wherein the health and beauty aid ingredient is selected from the group consisting of sun screen agents, fragrance oils, moisturizers, anti-perspirants, humectants, cosmetic oils and mixtures thereof.

9. A composition according to claim 1 which will release an excipient, a colorant, a preservative, a eiluent, or mixture thereof.

10. A health and beauty aid composition in gel form comprising an effective amount of one or more health and beauty aid components, about 80 to 99 wt. % of a hydrocarbon oil, and about 1 to 20 wt. % of a blend of at least two different polymer members selected from the group consisting of diblock copolymers and triblock copolymers, there being present at least one diblock copolymer and at least one triblock copolymer with said at least one diblock copolymer comprising 5 to 95 wt. % of said blend of at least two polymers and said at least one triblock copolymer comprising 5 to 95 wt. % of said blend of at least two polymers, said diblock copolymers and triblock copolymers being copolymers comprising block segments of styrene monomer units and rubber monomer units.

11. A composition according to claim 10, wherein the hydrocarbon oil is a white oil.

12. A composition according to claim 10, wherein the diblock copolymers and triblock copolymers are present in a ratio of from about 2:1 to 1:3.

13. A composition according to claim 10, wherein said health and beauty aid ingredient is present in an amount of about 0.001 to about 10 wt. %.

* * * * *